(12) United States Patent
Hedberg et al.

(10) Patent No.: US 8,620,432 B2
(45) Date of Patent: Dec. 31, 2013

(54) IDENTIFICATION OF PACING SITE

(75) Inventors: Sven-Erik Hedberg, Kungsängen (SE);
Nils Holmström, Järfälla (SE); John Gustafsson, Hägersten (SE); Andreas Blomqvist, Täby (SE); Andreas Karlsson, Solna (SE)

(73) Assignee: St. Jude Medical AB, Jarfalla (SE)

( * ) Notice: Subject to any disclaimer, the term of this patent is extended or adjusted under 35 U.S.C. 154(b) by 0 days.

(21) Appl. No.: 13/171,952

(22) Filed: Jun. 29, 2011

(65) Prior Publication Data

US 2012/0004700 A1 Jan. 5, 2012

Related U.S. Application Data

(60) Provisional application No. 61/383,537, filed on Sep. 16, 2010.

(30) Foreign Application Priority Data

Jun. 30, 2010 (EP) .................................... 10167991

(51) Int. Cl.
*A61N 1/00* (2006.01)
(52) U.S. Cl.
USPC ............................................... 607/27; 607/9
(58) Field of Classification Search
USPC ....................................................... 607/4–29
See application file for complete search history.

(56) References Cited

U.S. PATENT DOCUMENTS

| | | | |
|---|---|---|---|
| 7,142,919 B2 | 11/2006 | Hine et al. | |
| 7,305,266 B1 | 12/2007 | Kroll | |
| 7,330,759 B2 | 2/2008 | Militello | |
| 2006/0142811 A1 | 6/2006 | Militello | |
| 2008/0004667 A1 | 1/2008 | Arcot-Krishnamurthy et al. | |
| 2008/0249375 A1 | 10/2008 | Obel | |
| 2008/0249585 A1 | 10/2008 | Lippert et al. | |
| 2008/0306567 A1* | 12/2008 | Park et al. | 607/27 |
| 2009/0306732 A1 | 12/2009 | Rosenberg et al. | |
| 2010/0121397 A1 | 5/2010 | Cholette | |
| 2010/0125305 A1 | 5/2010 | Bornzin et al. | |

OTHER PUBLICATIONS

Ypenburg C et al., "Optimal Left Ventricular Lead Position . . . ", Journal of the American College of Card., vol. 52, No. 17, Oct. 21, 2008, pp. 1402 1409.

* cited by examiner

*Primary Examiner* — Scott Getzow

(57) ABSTRACT

An implantable medical device applies an electric signal over two electrodes and measures the resulting electric signal over a candidate pair of neighboring electrodes on a lead for a first heart ventricle or over a candidate electrode of the lead and a case electrode. An impedance signal is determined for each candidate pair or electrode based on the applied signal and the measured resulting signal. A time difference between start of contraction in a second ventricle and the timing of local myocardial contraction as identified from the impedance signal at the site of the candidate pair or electrode is determined for each candidate pair or electrode. An optimal pacing electrode is selected to correspond to one of the electrodes of the candidate pair having the largest time difference or the candidate electrode having largest time difference.

14 Claims, 7 Drawing Sheets

IDENTIFICATION OF PACING SITE

RELATED APPLICATION

The present application claims the benefit of provisional application 61/383,537, filed Sep. 16, 2010.

BACKGROUND OF THE INVENTION

1. Field of the Invention

The present embodiments generally relate to the field of implantable medical devices and in particular to identifying a suitable pacing site for such implantable medical devices.

2. Description of the Prior Art

It is generally regarded as important within the technical field of implantable medical devices (IMDs) to achieve an appropriate positioning of cardiac leads in or in connection with the ventricles of a heart for a patient. For instance, the position of a left ventricular coronary sinus lead has an impact on the outcome of cardiac resynchronization therapy (CRT) provided by an IMD to which the lead is connected. Most physicians implanting such leads in CRT patients, though, routinely go for a lateral or posterior-lateral vein that seems accessible for the particular patient. However, the most accessible vein might not be the most suitable pacing site from therapy point of view. A lot of focus has therefore been directed towards finding suitable pacing and implantation sites for cardiac leads and in particular left ventricular coronary sinus leads.

U.S. Pat. No. 7,142,919 discloses an IMD with a multi-electrode ventricular lead. Optimal pacing site is determined in connection with CRT by testing each of the electrodes of the multi-electrode ventricular lead as pacing electrode. Optimal pacing site and electrode is selected based on the output of a mechanical sensor, such as accelerometer or pressure sensor, attached epicardially on the left ventricle or from intracardiac electrograms (IEGM).

U.S. Pat. No. 7,330,759 relates to an IMD adapted for biventricular CRT stimulation and includes an impedance detection unit that is employed for selecting optimal biventricular stimulation. It is disclosed that optimal electrode position during implantation can be determined from determined intracardiac impedance or optimal stimulation electrode configuration can be determined following implantation from the intracardiac impedance. The relevant intracardiac impedance parameter employed in the site or electrode optimization is representative of the maximum acceleration to which the blood is exposed to in the heart.

US 2008/0249585 discloses an IMD suitable for CRT stimulation. The IMD has an impedance detection unit arranged for determining intracardiac impedance for the purpose of calculating a quality factor that is equal to the quotient of a first intracardiac impedance value determined for an intrinsic cardiac cycles sequence and a second intracardiac impedance value determined for a paced cardiac cycles sequence. The calculated quality factor can be used for determining optimal implantation site for a left ventricular lead by selecting the implantation site that gives the highest quality factor.

US 2008/0249375 relates to a pacing system analyzer (PSA) employed for selecting optimal lead position for a left ventricular lead during implantation. Impedance signals are recorded at different lead positions and processed to determine contractibility of the cardiac muscle, ejection fraction or pre-ejection time period. The position resulting in best contractibility, ejection fraction or pre-ejection time period is selected.

US 2008/0004667 relates to the selection of electrodes and pacing configuration parameters used to pace a heart chamber. A change in the hemodynamic state of the patient is detected and is used to determine a distribution of an electrical and/or mechanical parameter related to the contractile function of the heart chamber with respect to locations of multiple electrodes. A pacing output configuration is selected and the heart chamber is paced according to this pacing output configuration.

There is still a need for a technique that can be used to identify optimal pacing electrode and/or implantation site of a ventricular lead and in particular such a technique that does not require the usage of dedicated sensors or complex processing in the IMD.

SUMMARY OF THE INVENTION

It is an object of the invention to provide an implantable medical device configured to select optimal ventricular pacing electrode.

It is a particular objective to enable selection of a hemodynamically optimal pacing site for a ventricular lead.

These and other objectives are met by embodiments as disclosed herein.

Briefly an implantable medical device (IMD) in accordance with the invention has a lead connector configured to be electrically connected to a first ventricular lead having multiple electrodes and constructed to be implantable in or in connection with a first ventricle of a subject's heart and a second ventricular lead having at least one electrode and constructed to be implantable in or in connection with a second ventricle. A signal generator generates an electric signal that is applicable over two neighboring electrodes of the first ventricular lead or over an electrode of the first ventricular lead and a case electrode of the IMD. A signal sensing unit is configured to sense, for each candidate pair of neighboring electrodes or each candidate electrode of the first ventricular lead, a resulting electric signal over the candidate pair or the candidate electrode and the case electrode. The IMD has an impedance processor for determining, for each candidate pair or candidate electrode, an impedance signal representative of local myocardial contraction at the ventricular site of the candidate pair or candidate electrode based on the electric signal and the resulting electric signal sensed by the sensing unit for the candidate pair or candidate electrode. A time processor determines, for each candidate pair or candidate electrode, a time difference between start of contraction within the second ventricle and the timing of local myocardial contraction at the site of the candidate pair or electrode as identified from the impedance signal. An electrode selector is then configured to select a pacing electrode for the first ventricular lead to correspond to one of the electrodes of the electrode pair having the largest time difference or to correspond to the candidate electrode having the largest time difference.

An aspect of the embodiments relates to identifying a pacing site for a first ventricle of a subject's heart. The method comprises applying an electric signal over neighboring electrodes of a first ventricular lead for a first ventricle of the heart or over one of its electrodes and a case electrode of an IMD. A resulting electric signal is sensed for a candidate pair of neighboring electrodes of the first ventricular lead or over a candidate electrode of the lead and the case electrode. An impedance signal is determined based on the electric signal and the resulting electric signal and is representative of local myocardial contraction at the site of the first ventricle associated with the candidate pair or candidate electrode. The time difference between the identified start of contraction in a second ventricle of the heart and the timing of local myocardial contraction is determined based on the impedance signal. These steps are repeated for at least one other candidate pair or candidate electrode or for at least one other implantation site of the first ventricular lead. The optimal pacing site for the first ventricle then corresponds to the site of the candidate pair having the largest time difference, corresponds to the site of the candidate electrode having the largest time difference or corresponds to the site of the different implantation sites resulting in the largest time difference.

The embodiments enable identification and selection of a hemodynamically optimal pacing electrode and pacing site for a ventricular lead. Additionally, the embodiment can be used even for subjects suffering from electromechanical dissociation or other medical conditions that disturbs the time relationship between depolarization wave propagation and myocardial contraction.

DESCRIPTION OF THE PREFERRED EMBODIMENTS

Figure 3:
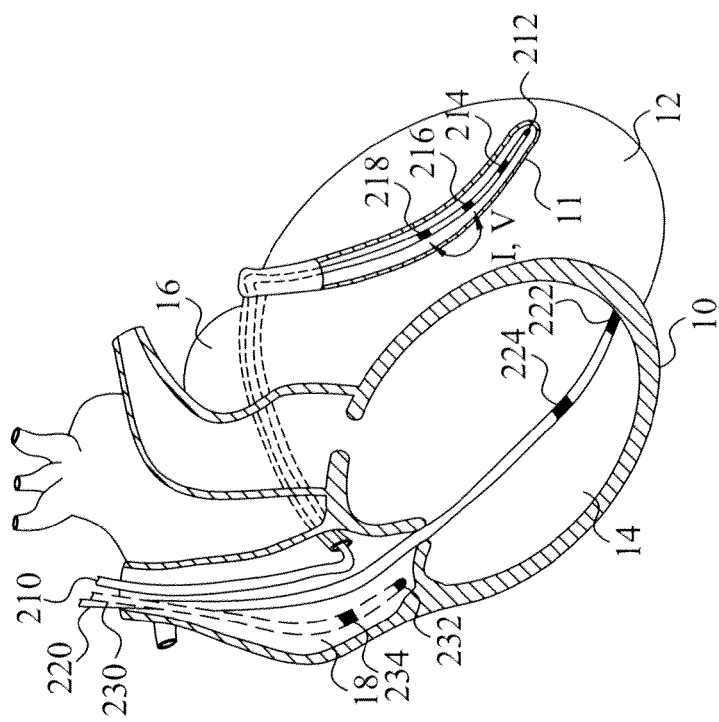
FIGS. 3-5 illustrate various embodiments determining impedance signals for candidate electrode pairs or candidate electrodes.

Throughout the drawings, the same reference numbers are used for similar or corresponding elements.

The present embodiments generally relate to implantable medical devices and in particular to selecting optimal ventricular pacing sites for such implantable medical devices.

The embodiments are based on the finding that pacing sites for pacing electrodes in or in connection with the heart of a subject has a significant impact on the cardiac function and cardiac output. For instance, cardiac resynchronization therapy (CRT) for heart failure patients would benefit a lot by achieving optimal positioning of pacing electrodes to thereby obtain synchronized contraction of the two ventricles and improved cardiac output.

The embodiments are based on using impedance measurements at different locations or sites in a given ventricle in order to detect the local myocardial contraction at the sites. The site that results in the largest time difference between start of contraction in the other ventricle and when local myocardial contraction occurs at the site is then selected as optimal pacing site. Thus the pacing site will then correspond to the hemodynamically optimal stimulation site at the given ventricle.

The inventors have further realized that using impedance in order to detect the occurrence of local myocardial contraction at different ventricular sites will result in a hemodynamically more optimal stimulation site as compared to indirect detection of contraction using other means, for instance in the form of registering the propagation of the depolarization wave over the ventricle. It is generally assumed that there is a fixed electromechanical relationship between the propagation of the depolarization wave over the myocardium of a ventricle and the timing of contraction of the ventricle. This might be true in healthy patients. However, many heart failure patients having an implantable medical device do not always have such a fixed electromechanical relationship. For instance, patients suffering from electromechanical dissociation, also denoted pulseless electrical activity or non-perfusing rhythm, can have a depolarization of the ventricle that does not result in any contraction of the ventricle or does not result in a coordinated contraction throughout the whole ventricle. There are several causes for such electromechanical dissociation including, for instance, hypovolemia, hypoxia, thrombosis, myocardial infarction, etc. Hence, conducting a search for optimal pacing sites based on sensing electric activity at different ventricular sites, for instance from an intracardiac electrogram (IEGM), can result in selecting a pacing site that is not hemodynamically optimal due to the lack of consistent electromechanical relationship between depolarization propagation and myocardial contraction for the patient. The embodiments do not have these problems since the pacing site optimization is based on the actual contraction at ventricular sites and not solely based on indirect contraction measurements using electrical activity of the ventricles.

Figure 1:
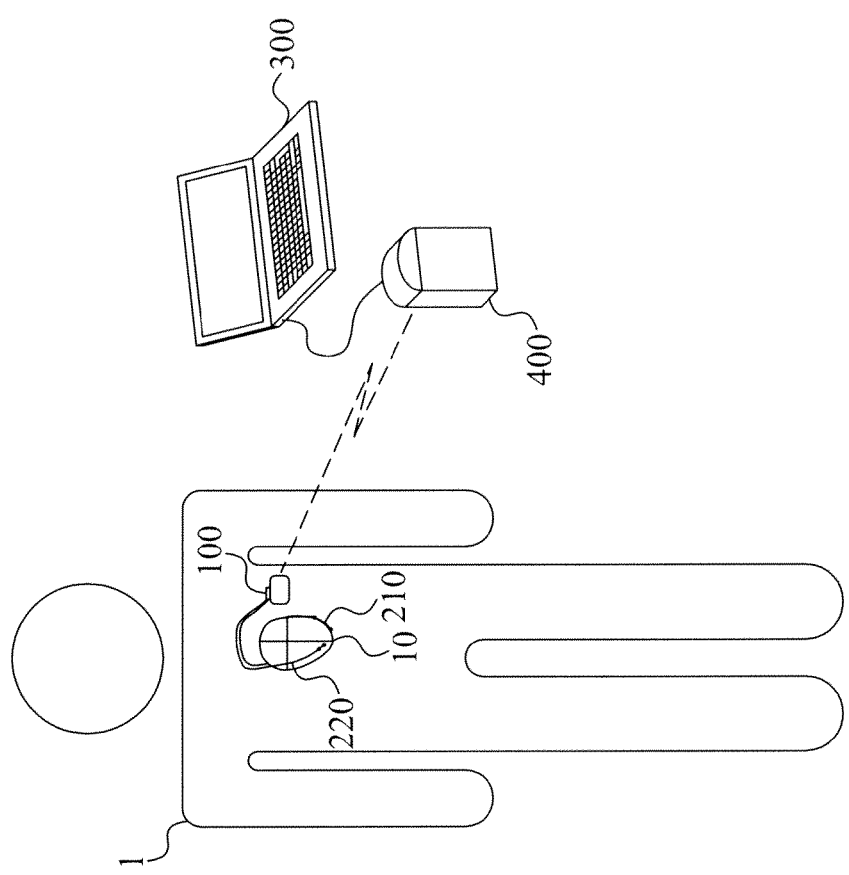
FIG. 1 is a schematic overview of a patient having an implantable medical device capable of conducting wireless communication with a data processing device.

FIG. 1 is a schematic overview of an implantable medical device (IMD) 100 according to the embodiments and a non-implantable data processing device 300. In the figure, the IMD 100 is illustrated implanted in a human patient 1 and as a device that monitors and/or provides therapy to the heart 10 of the patient 1. The patient 1 must not necessarily be a human patient but can instead be an animal patient, in particular a mammalian patient, in which an IMD 100 can be implanted. The IMD 100 can be in the form of a pacemaker, cardiac defibrillator or cardioverter, such as implantable cardioverter-defibrillator (ICD). The IMD 100 is, in operation, connected to two or more, two in the figure, cardiac leads 210, 220 inserted into different heart chambers, the right ventricle and left ventricle in the figure, or elsewhere provided in connection with a heart chamber.

FIG. 1 also illustrates an external data processing device 300, such as programmer or clinician's workstation, that can communicate with the IMD 100, optionally through a communication device 400 that operates similar to a base station on behalf of the data processing device 300. As is well known in the art, such a data processing device 300 can be employed for transmitting IMD programming commands causing a reprogramming of different operation parameters and modes of the IMD 100. Furthermore, the IMD 100 can upload diagnostic data descriptive of different medical parameters or device operation parameters collected by the IMD 100. Such uploaded data may optionally be further processed in the data processing device 300 before display to a clinician. In the light of the present embodiments, such diagnostic data can include impedance data, time interval data relating to contraction detection at ventricular sites, and/or other data relating to pacing site identification and selection.

Figure 2:
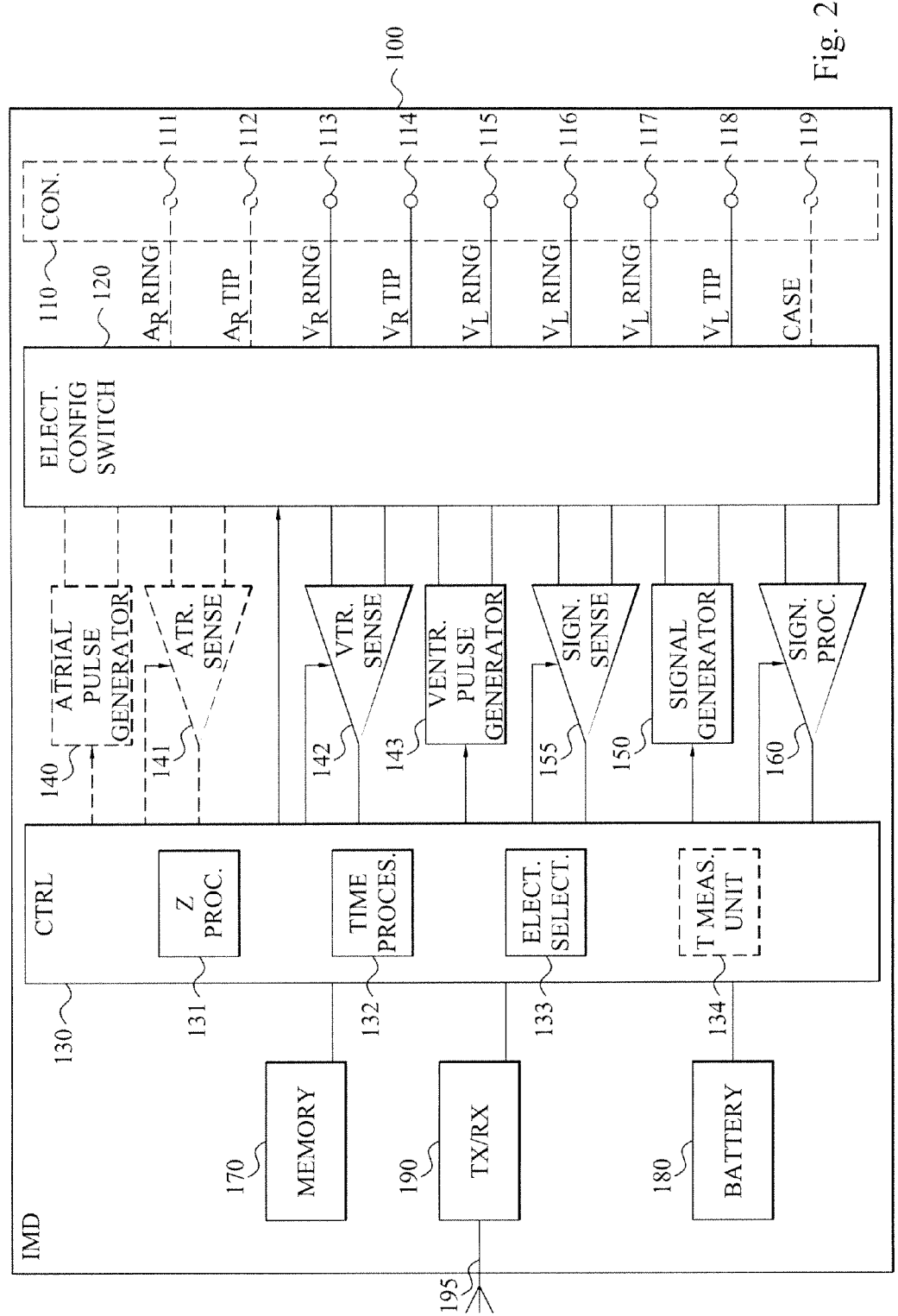
FIG. 2 schematically illustrates an embodiment of an implantable medical device.

FIG. 2 illustrates an embodiment of an IMD 100 suitable for delivering cardiac therapy to a heart of a subject. The figure is a simplified block diagram depicting various components of the IMD 100. While a particular multi-chamber device is shown in the figure, it is to be appreciated and understood that this is done merely for illustrative purposes. Thus, the techniques and methods described below can be implemented in connection with other suitably configured IMDs. Accordingly, the person skilled in the art can readily duplicate, eliminate, or disable the appropriate circuitry in any desired combination to provide an IMD capable of treating the appropriate heart chamber(s) with pacing stimulation and optionally also cardioversion and/or defibrillation.

The IMD 100 has a housing, often denoted as can or case in the art. The housing or a portion thereof can act as return electrode for unipolar leads, which is well known in the art. The IMD 100 also comprises a lead connector or input/output (I/O) 110 having, in this embodiment, a plurality of terminals 111-119. With reference to FIGS. 2 and 3, the lead connector 110 is configured to be, during operation in the subject body, electrically connectable to, in this particular example, a left ventricular lead 210, a right ventricular lead 220 and optionally also to a right atrial lead 230. The electrode connector 110 consequently comprises terminals 111, 112 that are electrically connected to matching electrode terminals of the atrial lead 230 when the atrial lead 230 is introduced in the lead connector 110. For instance, one of these terminals 112 can be designed to be connected to a right atrial tip terminal of the atrial lead 230, which in turn is electrically connected through a conductor running along the lead body to a tip electrode 232 present at the distal end of the atrial lead 230 in the right atrium 18 of the heart 10. A corresponding terminal 111 is then connected to a right atrial ring terminal of the atrial lead 230 that is electrically connected by another conductor in the lead body to a ring electrode 234 present in connection with the distal part of the atrial lead 230, though generally distanced somewhat towards the proximal lead end as compared to the tip electrode 232.

In an alternative implementation, the IMD 100 is not connectable to a right atrial lead 230 but instead to a left atrial lead configured for implantation in the left atrium 16. A further possibility is to have an IMD 100 with an electrode connector 110 having sufficient terminals to allow the IMD 100 to be electrically connectable to both a right atrial lead 230 and a left atrial lead.

The embodiments, however, do not necessarily have to use any atrial leads unless atrial sensing and pacing are desired. Thus, in such a case, the lead connector 110 is only connected to a right ventricular lead 220 and a left ventricular lead 210. The terminals 111, 112 of the lead connector 110 can then be omitted. In such a case, also the atrial pulse generator 140 and atrial sensing circuit 141 of FIG. 2, to be further described herein, can be omitted.

In order to support right chamber sensing and pacing, the lead connector 110 further has a right ventricular tip terminal 114 and a right ventricular ring terminal 113, which are adapted for connection to a right ventricular tip electrode 222 and a right ventricular ring electrode 224 of the right ventricular lead 220 implantable in the right ventricle 14, see FIG. 3.

The lead connector 110 is also connectable to a left ventricular lead 210. A left ventricular lead 210 is typically implanted in the coronary venous system 11 for safety reasons although implantation inside the left ventricle 12 has been proposed in the art. In the following, "left ventricular lead" 210 is used to describe a cardiac lead designed to provide sensing and pacing functions to the left ventricle 12 regardless of its particular implantation site, i.e. inside the left ventricle 12 or in the coronary venous system 11. The left ventricular lead 210 preferably also has a tip electrode 212 and at least one ring electrode 214, 216, 218 electrically connectable to corresponding terminals 115, 116, 117, 118 of the lead connector 110.

Figure 4:
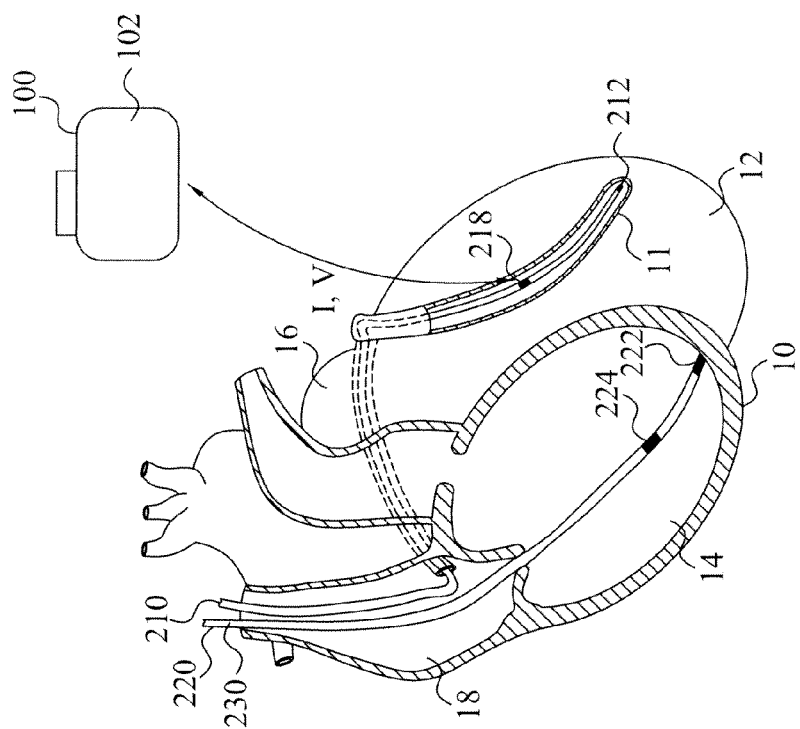

FIG. 3, the left ventricular lead 210 is exemplified as multi-electrode or multipolar lead and more correctly a quadropolar lead 210, i.e. having, in total, four electrodes 212-218. The embodiments are, however, not limited to using left ventricular leads of multipolar type, i.e. leads having three or more electrodes. In contrast, the left ventricular lead 210 can alternatively be a bipolar lead having a tip electrode 212 and one ring electrode 218 as illustrated in FIG. 4. The number of terminals of the lead connector 110 should then be reduced to match the number of electrodes of the left ventricular lead 210.

The right ventricular lead 220 could also be a multipolar lead, such as quadropolar lead. The lead connector 110 would then need to comprise at least three, such as four, terminals to be connected to matching electrode terminals at the proximal end of the multipolar right ventricular lead. Also a combination of multipolar right and ventricular leads are possible and within the scope of the embodiments.

In an aspect of the embodiments relating to the implantable medical device 100, the lead connector 110 is electrically connectable to a first ventricular lead having multiple, i.e. at least two, electrodes and a second ventricular lead having at least one electrode. The first ventricular lead is constructed to be implanted in or in connection with a first ventricle of the heart and the second ventricular lead is correspondingly constructed to be implanted in or in connection with a second ventricle of the heart. In such a case, the identification of optimal pacing site and electrode for the heart is conducted in the first ventricle. The second ventricular lead is then employed as reference lead as is further described herein.

If any of the cardiac leads 210, 220, 230 comprises a shock electrode the lead connector 110 has a matching terminal configured to be electrically connectable to the shock electrode.

The housing can act as return electrode as mentioned above. In such a case, the lead connector 110 can have a dedicated terminal 119 connected to the housing or the case electrode 102 of the housing illustrated in FIGS. 4 and 5.

The IMD 100 as illustrated in FIG. 2 comprises an optional atrial pulse generator 140 and a ventricular pulse generator 143 that generate pacing pulses for delivery by the optional atrial lead(s) and the ventricular leads preferably through an electrode configuration switch 120.

It is understood that in order to provide stimulation therapy in different heart chambers, the atrial and ventricular pulse generators 140, 143 may include dedicated, independent pulse generators, multiplexed pulse generators, or shared pulse generators. The pulse generators 140, 143 are controlled by a controller 130 via appropriate control signals, respectively, to trigger or inhibit the stimulating pulses.

The controller 130 is preferably in the form of a programmable microcontroller 130 that controls the operation of the IMD 100. The controller 130 typically includes a microprocessor, or equivalent control circuitry, designed specifically for controlling the delivery of pacing therapy, and may further include RAM or ROM memory, logic and timing circuitry, state machine circuitry, and I/O circuitry. Typically, the controller 130 is configured to process or monitor input signal as controlled by a program code stored in a designated memory block. The type of controller 130 is not critical to the described implementations. In clear contrast, any suitable controller may be used that carries out the functions described herein. The use of microprocessor-based control circuits for performing timing and data analysis functions are well known in the art.

The controller 130 further controls the timing of the stimulating pulses, such as pacing rate, atrioventricular interval (AVI), atrial escape interval (AEI) etc. as well as to keep track of the timing of refractory periods, blanking periods, noise detection windows, evoked response windows, alert intervals, marker channel timing, etc.

A preferred electronic configuration switch 120 includes a plurality of switches for connecting the desired terminals 111-119 to the appropriate I/O circuits, thereby providing complete electrode programmability. Accordingly, the electronic configuration switch 120, in response to a control signal from the controller 130, determines the polarity of the stimulating pulses (e.g., unipolar, bipolar, combipolar, etc.) by selectively closing the appropriate combination of switches (not shown) as is known in the art.

An optional atrial sensing circuit or detector 141 and a ventricular sensing circuit or detector 142 are also selectively coupled to the optional atrial lead(s) and the ventricular leads through the switch 120 for detecting the presence of cardiac activity in the heart chambers. Accordingly, the atrial and ventricular sensing circuits 141, 142 may include dedicated sense amplifiers, multiplexed amplifiers, or shared amplifiers. The switch 120 determines the "sensing polarity" of the cardiac signal by selectively closing the appropriate switches, as is also known in the art. In this way, the clinician may program the sensing polarity independent of the stimulation polarity. The sensing circuits are optionally capable of obtaining information indicative of tissue capture.

Each sensing circuit 141, 142 preferably employs one or more low power, precision amplifiers with programmable gain and/or automatic gain control, band-pass filtering, and a threshold detection circuit, as known in the art, to selectively sense the cardiac signal of interest.

The outputs of the atrial and ventricular sensing circuits 141, 142 are connected to the controller 130, which, in turn, is able to trigger or inhibit the atrial and ventricular pulse generators 140, 143, respectively, in a demand fashion in response to the absence or presence of cardiac activity in the appropriate chambers of the heart.

Furthermore, the controller 130 is also capable of analyzing information output from the sensing circuits 141, 142 and/or a data acquisition unit 160 to determine or detect whether and to what degree tissue capture has occurred and to program a pulse, or pulse sequence, in response to such determinations. The sensing circuits 141, 142, in turn, receive control signals over signal lines from the controller 130 for purposes of controlling the gain, threshold, polarization charge removal circuitry, and the timing of any blocking circuitry coupled to the inputs of the sensing circuits 141, 142 as is known in the art.

According to the embodiments cardiac signals are applied to inputs of the data acquisition unit 160 connected to the electrode connector 110. The data acquisition unit 160 is preferably in the form of an analog-to-digital (ND) data acquisition unit 160 configured to acquire intracardiac electrogram (IEGM) signals, convert the raw analog data into a digital signal, and store the digital signals for later processing and/or transmission to the programmer by a transceiver 190. The data acquisition unit 160 is coupled to the atrial lead and/or the ventricular leads through the switch 120 to sample cardiac signals across any pair of desired electrodes.

Figure 5:
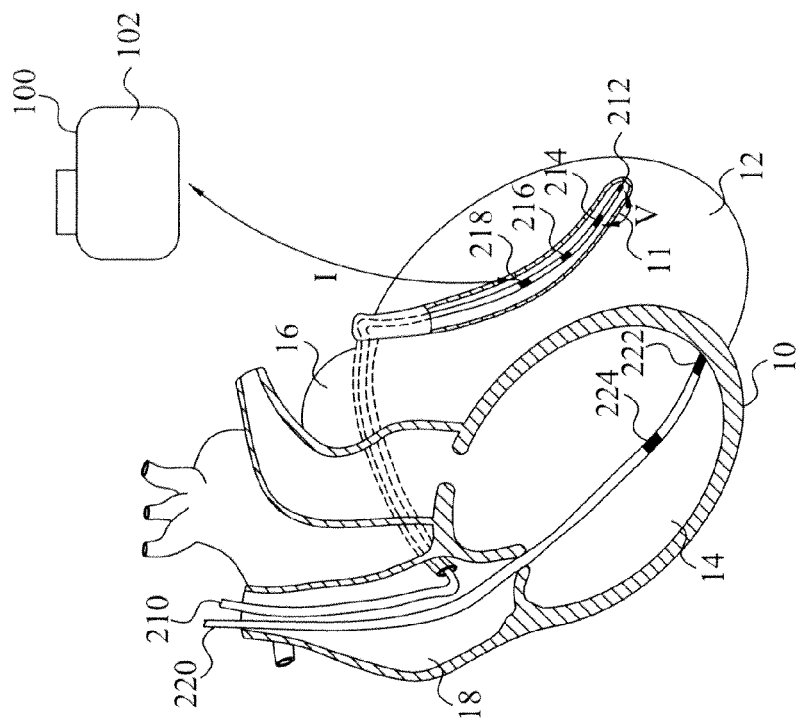

The IMD 100 also has a signal generator 150 connectable to two of the terminals 113-119 preferably through the switch 120. The signal generator 150 is configured to generate an electric signal that is applicable over two neighboring electrodes of a first ventricular lead or over an electrode of the first ventricular lead and the case electrode. The expression "neighboring electrodes" refers herein to adjacent electrodes as positioned along the ventricular lead. For instance, in FIG. 3 the tip electrode 212 and the first ring electrode 214 of the left ventricular lead 210 are neighboring electrodes, the first 214 and second 216 ring electrodes are neighboring electrodes and the second 216 and third 218 ring electrodes are neighboring electrodes. Thus, if the first ventricular lead is the left ventricular lead the electric signal generated by the signal generator 150 can be applied, preferably through the switch 120, to terminals 117, 118 or terminals 116, 117, or terminals 115, 116 or to terminal 119 and any of the terminals 115-118. FIGS. 3-5 illustrate these different concepts. In the figures, the double arrow line marked as I represents the applied electric signal. In FIG. 3, the electric signal is applied between two neighboring electrodes 216, 218, whereas in FIGS. 4 and 5 the electric signal is applied between the case electrode 102 and one of the electrodes 218 of the left ventricular lead 210.

The electric signal is preferably an AC current having a defined time-dependent voltage/current profile. The electric signal is preferably a sub-threshold electric signal implying that it is not intended to trigger capture of the myocardium when applied to the heart. This is in clear contrast to the pacing pulses generated by the atrial 140 and ventricular 143 pulse generator.

In FIG. 3 the signal generator 150 has been illustrated as a stand-alone signal generator 150 controlled by the controller 130. In an alternative approach, the relevant sub-threshold AC signal could instead be generated by the ventricular pulse generator 143, thereby relaxing the need for a further generator 150 of the IMD 100. In such a case, the controller 130 controls the ventricular pulse generator 143 to generate the electric signal having characteristics, i.e. duration and amplitude, which generally differ from the pacing pulses otherwise generated by the pulse generator 143.

A signal sensing unit 155 is implemented preferably connected to the switch 120 and thereby to two terminals connected to two electrodes. The sensing unit 155 is configured to sense, for each candidate pair of neighboring electrodes of the first ventricular lead or for each candidate electrode of the first ventricular lead, a resulting electric signal captured over the candidate pair of neighboring electrodes or over the candidate electrode and the case electrode. Thus, in a preferred embodiment each candidate pair of neighboring electrodes or each single candidate electrode of the first ventricular lead is tested and used to capture the resulting electric signal.

In a particular embodiment, a given candidate pair or candidate electrode is first tested and used to capture the resulting electric signal during at least one cardiac cycle. Thereafter, another candidate pair or candidate electrode is employed to capture the resulting electric cycle during at least one other cardiac cycle. The signal sensing unit 155 and the switch 120 thereby successively go through and test each candidate pair or candidate electrode of the first ventricular lead. As a consequence, the signal generator 150 is then preferably configured to generate and apply the electric signal over multiple cardiac cycles to thereby allow each of the candidate pairs or candidate electrodes to capture the resulting electric signal one at a time. In such a case, the conditions when testing the different candidate pairs or electrodes should preferably be as close to equal as possible. This can be controlled by determining the heart rate in connection with sensing resulting electric signal using the IEGM signal from data acquisition unit 160. The controller 130 could then be configured to only use and further process electric signals if the heart rate is constant or does not differ more that a defined amount for the different time periods when the candidate pairs or candidate electrodes are tested. This approach therefore can be regarded as using time multiplexing for the electric signal sensing.

In an alternative approach the electric signal generated by the signal generator 150 is a multi-frequency signal comprising multiple frequency components. The candidate pairs or candidate electrodes then use different measurement frequencies so that all candidate pairs or candidate electrodes can capture the resulting electric signal in parallel but the signal sensing unit 155 extracts different frequency components from the resulting electric signal from different candidate pairs or candidate electrodes.

FIGS. 3-5 illustrate this sensing of the resulting electric signal by the double arrow line marked with V. In FIG. 3, the same electrode pair 216, 218 that was used for applying the electric signal is also used for sensing or capturing the resulting electric signal. This corresponds to so-called bipolar impedance vector as is further described herein. In FIG. 4 the electric signal is applied over and the resulting electric signal is captured over the same candidate electrode 218 and the case electrode 102. This is denoted unipolar impedance vector in the art. A further alternative is shown in FIG. 5, where the electric signal is applied over one electrode 218 of the first ventricular lead 210 and the case electrode 102 and the resulting electric signal is sensed over a candidate pair of electrodes 212, 214, which does not include the electrode 218 used together with the case electrode 102 for signal application. The result will be a so-called quadropolar impedance vector.

The resulting electric signal is preferably a resulting AC signals originating from at least a portion of the heart. This sensed AC signals is further generated due to the applied AC signal generated by the signal generator 150.

An impedance processor 131 is implemented in the IMD 100 and configured to determine, for each candidate pair or for each candidate electrode, an impedance signal representative of local myocardial contraction at the site of the first ventricle associated with the candidate pair or candidate electrode based on the electric signal generated by the signal generator 150 and the resulting electric signal sensed by the signal sensing unit 155 for the candidate pair or the candidate electrode. Thus, a respective impedance signal that represents and captures the local myocardial contraction at the site where the candidate pair or candidate electrode is implanted is determined by the impedance processor 131. The impedance signal is typically in the form of a sample sequence where each sample includes a single impedance value or multiple values in the case of complex impedance, i.e. real or imaginary value or amplitude and phase angle, corresponding to the impedance determined for the local site of the candidate pair or candidate electrode at the time point corresponding to the particular sample.

In an embodiment, the impedance processor 131 generates respective impedance signals based on the current of the electric signal and the measured or sensed voltage of the resulting electric signals according to techniques well known in the art.

In a particular embodiment, the impedance processor 131 determines respective cardiogenic impedance signals as bandpass filtered versions of the calculated impedance signal in order to remove or at least suppress the respiratory contribution to the impedance signal. The cardiogenic impedance signal is further preferably characterized by not having any DC component, i.e. its average value is zero.

In order to reduce the effect or noise or other disturbing sources that might occur during a cardiac cycle, such as local micro-movement of the first ventricular lead, the impedance processor 131 can optionally determine the impedance signal as representing the average or median impedance for multiple cardiac cycles per candidate pair or electrode. In such a case, the signal sensing unit 155 senses the resulting electric signal over the candidate pair or candidate electrode and case electrode during multiple, preferably consecutive, cardiac cycles. The average or median impedance value or values is or are then computed for each sample for a cardiac cycle to thereby get an impedance signal extending over at least one cardiac cycle and where each signal sample value(s) correspond(s) to the average or median impedance for the relevant candidate pair or candidate electrode.

A time processor 132 of the IMD is configured to determine, for each candidate pair or each candidate electrode, a time difference between start of contraction within the second ventricle and a timing of the local contraction at the site associated with the candidate pair or candidate electrode as identified from the impedance signal for that candidate pair or candidate electrode.

In an embodiment, the start of contraction within the second ventricle is identified by a signal processing unit connected to the lead connector 110 and based on signals sensed by the second ventricular lead. In a particular embodiment, this signal processing unit corresponds to the data acquisition unit 160. Thus, in such a case the relevant signal sensed by the second ventricular lead is the electrical activity of the second ventricle and the signal is advantageously an IEGM signal. Start of contraction can easily be identified in such an IEGM signal as corresponding to the timing of the QRS-complex, Q-wave or R-wave.

In another embodiment, the signal processing unit corresponds to the impedance processor 131. In such a case, the signal generator 150 also generates a signal that is applied over two electrodes of the second ventricular lead or over an electrode of the second ventricular lead and the case electrode. The signal sensing unit 155 senses the resulting electric signal over two electrodes of the second ventricular lead or over an electrode of the second ventricular lead and the case electrode. The impedance processor 131 generates an impedance signal from which the contraction in the second ventricle can be identified. The impedance signal is preferably a cardiogenic impedance signal from a unipolar, bipolar, tripolar or quadropolar impedance vector.

Thus, the time processor 132 thereby determines a time difference or time value for each candidate pair or candidate electrode of the first ventricular lead. In this embodiment, the time difference defines the time interval from when contraction is started in the right ventricle as identified from the IEGM signal or an impedance signal as mentioned above, to when contraction of the myocardium is detected at the site in the first ventricle at which the candidate pair or candidate electrode is positioned based on the impedance signal determined for the candidate pair or candidate electrode.

Figure 9:
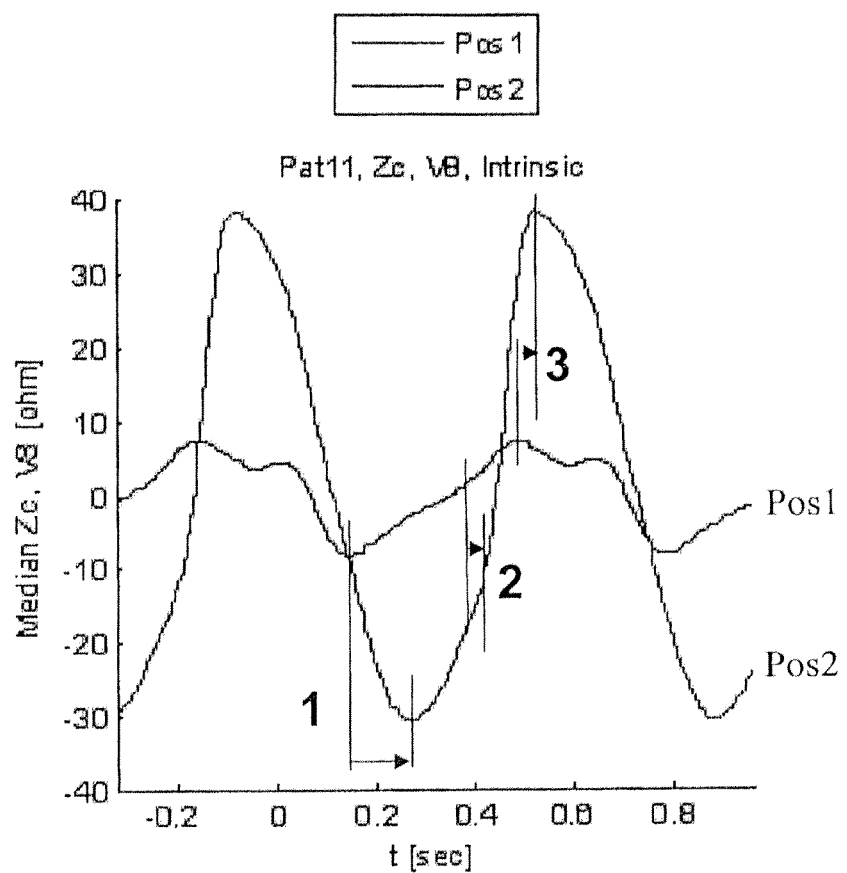
FIG. 9 is a diagram illustrating cardiogenic impedance measured for two different left ventricular sites for intrinsic heart cycles.
Figure 10:
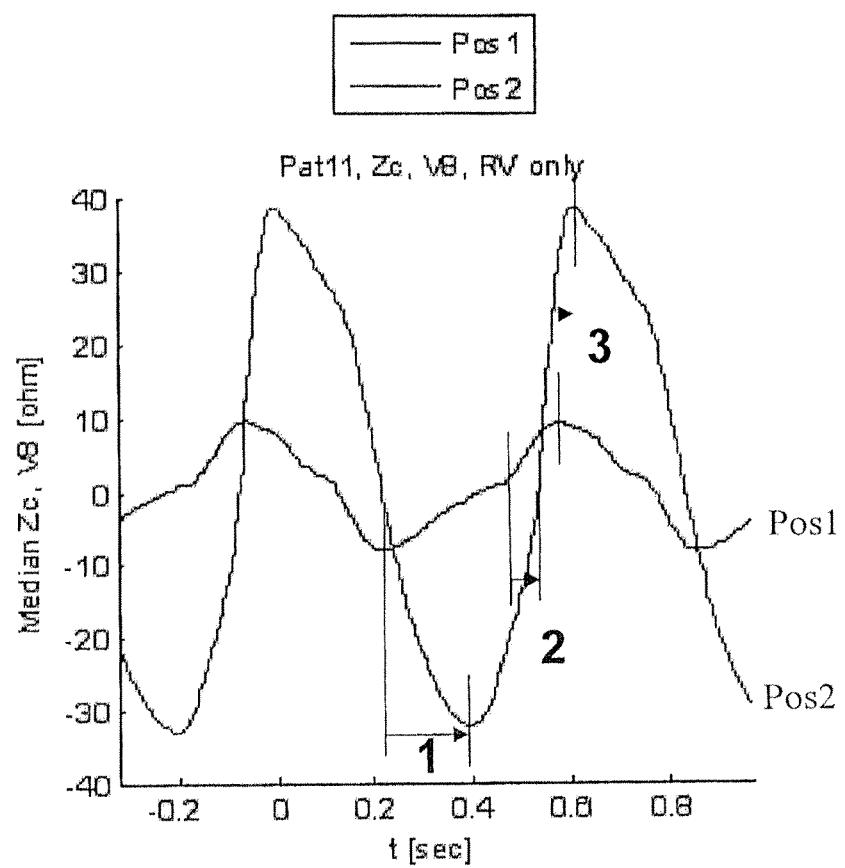
FIG. 10 is a diagram illustrating cardiogenic impedance measured for two different left ventricular sites for heart cycles with right ventricular pacing.

Start of contraction is preferably identified in the impedance signal as a minimum, preferably global minimum, during the cardiac cycle. FIGS. 9 and 10 illustrate two diagrams plotting an impedance signal in terms of median cardiogenic impedance from a bipolar impedance vector as disclosed in FIG. 3. Both figures illustrate the impedance signal at two different positions (Pos 1 and Pos 2) within the left ventricle. FIG. 9 represents the result for intrinsic cardiac cycles, whereas FIG. 10 illustrates the corresponding impedance signals for paced cardiac cycles with pacing conducted in the right ventricle. The features marked as 1 in the figures represent start of contraction in the left ventricle and coincide with the global impedance minimum. Features 2 and 3 mark inflection point and maximum contraction, respectively. As is seen from the figures, local myocardial contraction occurs at a later point in time at the second position (Pos 2) as compared to the first position (Pos 1) when determined from a reference time point corresponding to start of contraction in the right ventricle (t=0 s). In the experiment illustrated in FIG. 9, the time from start of contraction in the right ventricle, corresponding to right ventricular sensing, to the first mechanical contraction increased from 0.14 to 0.27 s. In the experiment of FIG. 10 the corresponding time difference increased from 0.22 to 0.39 s.

In a particular embodiment, the time processor 132 therefore parses through all the impedance samples of the (average or median) impedance signal for a cardiac cycle for each of the candidate pairs or candidate electrodes. The timing of local myocardial contraction is then identified as the impedance sample that has the smallest impedance value. The time processor 132 therefore preferably identifies one such impedance sample per candidate pair or candidate electrode. The sample numbers of the impedance samples can then be used directly as time parameter or can be converted to a value in seconds based on the sampling frequency used by the impedance processor 131. The time differences are then determined, in an embodiment, by noting the sample number in the IEGM signal or impedance signal corresponding to start of contraction in the second ventricle and optionally converting that into a value in second and then calculating how much time has passed until the local contraction is detected at the different candidate pairs or candidate electrodes.

In another embodiment applicable to paced cardiac cycles, the start of contraction in the second ventricle is defined based on the timing of generating and, above all, applying a pacing pulse to the second ventricle using one or more electrodes of the second ventricular lead. The applied pacing pulse will then trigger contraction of the second ventricle. This means that this embodiment does not require, but can use if desired, a signal processing unit in order to identify the start of contraction within the second ventricle. In clear contrast, the start of contraction of the second ventricle is defined based on the timing or time point of generating a pacing pulse to be applied to the second ventricle or more preferably, if significantly different from the time point of generating the pacing pulse, the timing or time point of applying the pacing pulse to the second ventricle by means of the second ventricular lead.

The time processor 132 then determines, for each candidate pair or each candidate electrode of the first ventricular lead, a time difference between the timing of generating/applying a pacing pulse to the second ventricle, as representative of the start of contraction within the second ventricle, and the timing of the local myocardial contraction at the site associated with the candidate pair or the candidate electrode at the first ventricle.

An electrode selector 133 of the IMD 100 processes the determined time differences from the time processor 132 and identifies the candidate pair or candidate electrode that resulted in the largest time difference. The pacing electrode to use in the left ventricle is then selected from one of the electrodes of the candidate pair having largest time difference or corresponding to the candidate electrode having largest time difference.

In the embodiment illustrated in FIG. 3, the signal generator 150 generates the electric signal, which is first applied over a first candidate pair, such as tip electrode 212 and first ring electrode 214. The signal sensing unit 155 senses the resulting electric signal over these two electrodes 212, 214 and the impedance processor 131 calculates the impedance signal for this first candidate pair. In an embodiment, simultaneously or at least partly in parallel with the measurements in the left ventricle 12, the data acquisition unit 160 registers the electrical activity in the right ventricle 14 by means of the right ventricular lead 220. The time processor 132 processes the IEGM signal and the impedance signal to determine the time difference between start of contraction in the right ventricle 14 and the timing of local myocardial contraction in the left ventricle 12 at the site around the electrodes 212, 214. Alternatively and for paced cardiac cycles, the time processor 132 defines the start of contraction in the right ventricle 14 based on information of the timing of pacing pulse generation/application for the right ventricle 14. This procedure is then repeated with ring electrodes 214, 216 as second candidate pair and ring electrodes 216, 218 as third candidate pair. Assume that candidate pair with electrodes 216, 218 resulted in the largest time difference. In such a case, the electrode selector 133 selects one of these two electrodes 216, 218 as pacing electrode for the left ventricle 12.

In FIG. 4 candidate electrodes 212, 218 are tested one by one and not as candidate pairs. This means that the electric signal application and resulting signal sensing is conducted over the case electrode 102 and a candidate electrode 212, 218. The candidate electrode that resulted in the largest time difference is then used as pacing electrode in the left ventricle 12.

In FIG. 5 the electric signal is applied over the case electrode 102 and one of the electrodes 218 of the left ventricular lead 210. The resulting electric signal is sensed over a candidate pair of two other electrodes 212, 214 of the left ventricular lead 218. For instance, if signal application uses ring electrode 218 as illustrated in the figure, signal sensing can be conducted of the neighboring electrodes 212, 214 and/or the electrodes 214, 216. If signal sensing is to be conducted over the neighboring electrodes 216, 218 the electric signal have to be applied over the case electrode 102 and any of electrodes 212, 214. In similarity to the embodiment in FIG. 3, the candidate pair having the largest time difference will be identified by the electrode selector 133 and one of the two electrodes in the identified pair is used as pacing electrode.

In FIGS. 3-5 selecting the pacing site and pacing electrode in connection with the left ventricle has been disclosed. Thus, in such a case the left ventricle constitutes the previously mentioned first ventricle and the right ventricle will be the second ventricle. This is particularly advantageous for patients suffering from left bundle branch block (LBBB). If the patient is instead suffering from right bundle branch block (RBBB) it is advantageous to find the optimal pacing site and electrode of the right ventricle. The discussion above is then basically conducted in the same way but then the candidate pair or candidate electrodes are present on the right ventricular lead the time differences are determined from start of contraction in the left ventricle up to timing of local contraction at the different right ventricular sites of the candidate pairs or candidate electrodes.

If the electrode selector 133 identifies a candidate pair that has the largest time difference, then there is actually a choice between two electrodes that could be used as pacing electrode. In an embodiment, the electrode selector 133 simply selects one of these two electrodes without any further evaluation.

In another embodiment, a more refined procedure is started with these two electrodes as candidate electrodes. In such a case, unipolar measurements as disclosed in FIG. 4 can be conducted with these two electrodes in order to determine for which of these two electrodes that local myocardial contraction occurs latest within a cardiac cycle. However, it is generally regarded that there will be no significant difference in the timings of local cardiac contraction between these two neighboring electrodes unless they are positioned quite a distance from each other on the ventricular lead. In such a case, any of the electrodes can be selected or a further test as described below can be used.

A further embodiment uses a threshold measuring unit 134 that is configured to measure respective pacing thresholds for the two electrodes of the selected electrode pair. As is well known in the art, threshold measurements involves estimating the minimum voltage of the applied pacing pulse that is required in order to induce capture by the myocardium when using a given pacing electrode. This threshold value can be different for different electrodes, to thereby reflect variations in local environment, such as thickness of surrounding connective tissue, in the vicinity of the electrodes. In such case, the electrode selector 133 preferably selects the electrode of the identified candidate pair that has the lowest pacing threshold as estimated by the threshold measuring unit 134. A lower pacing threshold implies that less energy is drained from a battery 180 of the IMD 100 in order to generate the pacing pulses as compared to having an electrode with comparatively higher pacing threshold. Alternatively, the operation of the threshold measuring unit 134 can be at least partly implemented by the ventricular sensing unit 142.

Another feature that can be tested and used to select pacing electrode from the identified candidate pair with the largest time difference is from R-wave testing. R-wave testing is well known in the art and can be conducted by means of the data acquisition unit 160.

Also a combination of the above presented features can be used in order to identify the most suitable pacing electrode of the identified candidate pair having the largest time difference.

The optimal pacing site and pacing electrode can sometimes differ between intrinsic cardiac cycles and paced cardiac cycles. Intrinsic cardiac cycles imply that there is no corresponding pacing in the second ventricle and paced cardiac cycles imply that pacing pulses are applied to the second ventricle. In such a case, the IMD 100 can be operated to selecting an optimal pacing electrode to be used for pacing in the first ventricle when no pacing is applied to the second ventricle and select an optimal pacing electrode to be used for pacing the first ventricle when pacing is also conducted in the second ventricle. This means that the ventricular pulse generator 143 will be active during paced cardiac cycles but not according to intrinsic cardiac cycles when optimal pacing electrodes are to be determined.

The signal sensing unit 155 is then configured to sense, for each candidate pair or candidate electrode, a first resulting electric signal for at least one paced cardiac cycle and sense a corresponding second resulting electric signal for at least one intrinsic cardiac cycle. The impedance processor 131 generates a first impedance signal for the paced case and a second impedance signal for the intrinsic case for each candidate pair or candidate electrode. The time processor 132 then determined a paced time difference between the start of contraction in the second ventricle and a timing of local contraction in the first ventricle for paced cardiac cycles and a spontaneous time difference between start of contraction in the second ventricle and a timing of local contraction in the first ventricle for intrinsic cardiac cycles for each of the candidate pairs or candidate electrodes. The electrode selector 133 selects a pacing electrode to use for paced cardiac cycles for the first ventricle corresponding to one of the electrodes of the candidate pair having largest paced time difference or corresponding to the candidate electrode having the largest paced time difference. The electrode selector 133 further selects a pacing electrode to use for intrinsic cardiac cycles corresponding to one of the electrodes of the candidate pair having largest spontaneous time difference or corresponding to the candidate electrode having the largest spontaneous time difference.

Different triggers for initiating determination of optimal pacing electrode are possible. For instance, the IMD 100 can conduct the above described procedure in order to identify optimal pacing electrode in connection with implantation of the IMD 100 in the subject body. Alternatively, the procedure can be triggered at a later point in time, such as in connection with a follow up or visit to the subject's physician. In such a case, the physician can transmit a command to the IMD 100 using the data processing unit and communication unit illustrated in FIG. 1. The command will be captured by an antenna 195, such as RF antenna, connected to a transceiver 190 or receiver of the IMD 100. The command is forwarded to the controller 130 that activates the relevant units of the IMD 100 in order to collect the data needed to select optimal pacing electrode.

In another embodiment, the IMD 100 and controller 100 can be programmed to periodically perform a search for optimal pacing electrodes since it might be possible that optimal pacing electrode changes over time due to non-stable conditions to the subject's heart. It is expected that such a procedure does not need to be conducted very often but typically once per month, once every second or third month, once or twice per year or even more seldom.

It could also be possible to have a conditioned trigger so that the IMD 100 will start a new procedure to identify optimal pacing electrode upon detection of one or more defined cardiac events. Such cardiac events could be to handle a medical condition that is known to possible affect the depolarization propagation over the ventricles, the mechanical contraction and/or electromechanical relationship of a ventricle, such as a myocardial infarct.

The controller 130 of the IMD 100 is typically coupled to a memory 170 by a suitable data/address bus, wherein the programmable operating parameters used by the controller 130 are stored and modified, as required, in order to customize the operation of the IMD 100 to suit the needs of a particular patient. Such operating parameters define, for example, time threshold, pacing pulse amplitude, pulse duration, electrode polarity, rate, sensitivity, automatic features, and time interval between pacing pulse of an applied pacing pulse sequence.

The memory 170 may also advantageously store diagnostic data collected by the IMD 100. The diagnostic data include the IEGM signal from the data acquisition unit 160, the impedance signal from the impedance processor 131 and the electrode selection data from the electrode selector 133.

Advantageously, the operating parameters of the IMD 100 may be non-invasively programmed into the memory 170 through the transceiver 190 in communication via a communication link with the previously described communication unit of the programmer. The controller 130 activates the transceiver 190 with a control signal. The transceiver 190 can alternatively be implemented as a dedicated receiver and a dedicated transmitter connected to separate antennas or a common antenna, preferably a radio frequency (RF) antenna 195.

The IMD 100 additionally includes a battery 180 that provides operating power to all of the circuits shown in FIG. 2.

In FIG. 2 the impedance processor 131, the time processor 132, the electrode selector 133 and the optional threshold measuring unit 134 have been exemplified as being run by the controller 130.

These units can then be implemented as a computer program product stored on the memory 170 and loaded and run on a general purpose or specially adapted computer, processor or microprocessor, represented by the controller 130 in the figure. The software includes computer program code elements or software code portions effectuating the operation of impedance processor 131, the time processor 132, the electrode selector 133 and the optional threshold measuring unit 134. The program may be stored in whole or part, on or in one or more suitable computer readable media or data storage means that can be provided in an IMD 100.

In an alternative embodiment, impedance processor 131, the time processor 132, the electrode selector 133 and the optional threshold measuring unit 134 are implemented as hardware units either forming part of the controller 130 or provided elsewhere in the IMD 100.

Figures 11, 12:
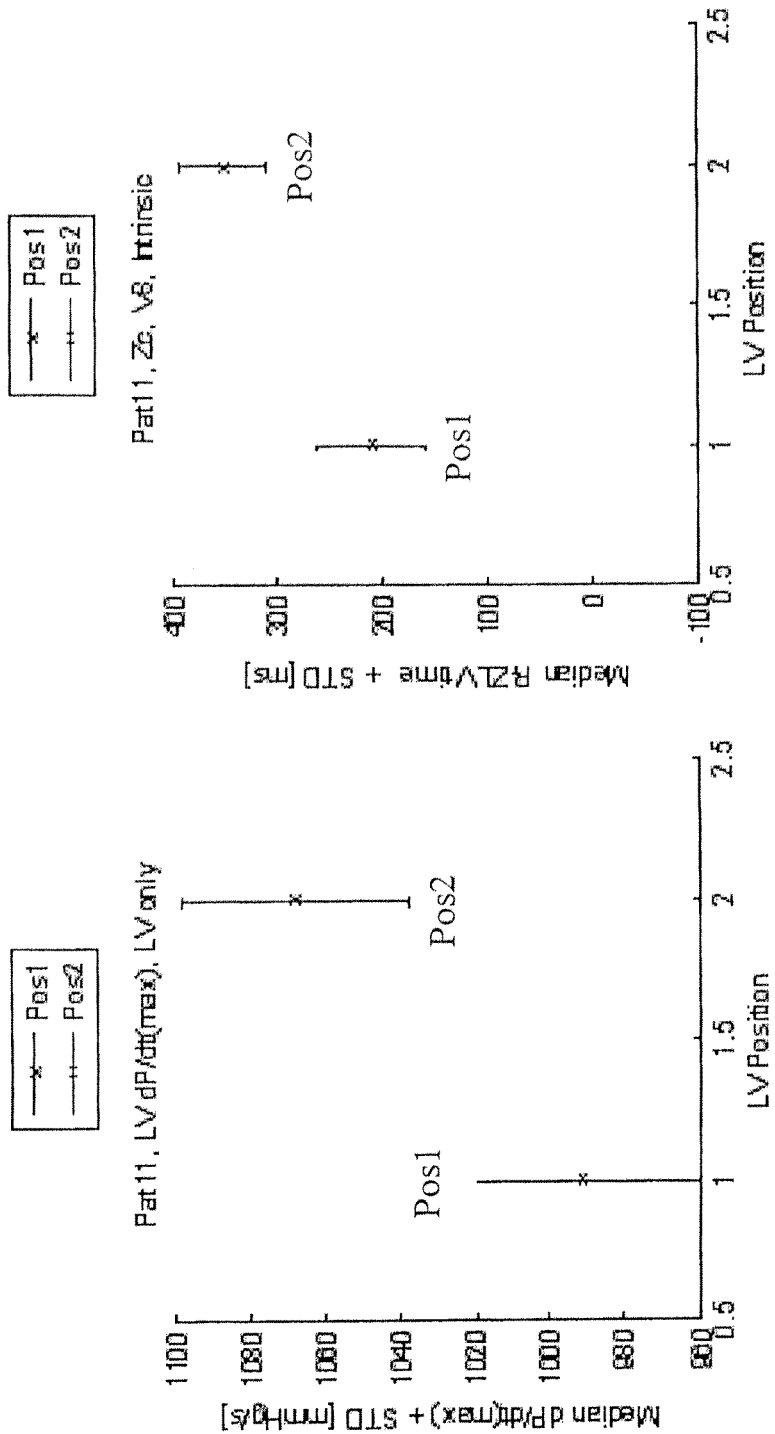
FIG. 11 is a diagram illustrating median left ventricular dP/dt(max) for the experiment of FIG. 9.
FIG. 12 is a diagram illustrating median time difference determined for the experiment of FIG. 9.

Human tests have been conducted and the results are presented in FIGS. 9-12. The data originates from heart failure patients with left bundle branch block. The data has been extracted by means of Promote device during implantation of a CRT device. The pressure data from left ventricle has been recorded by a Radi Pressure Wire. FIGS. 9 and 10 have previously been described and disclose the impedance signal as determined for two ventricular sites using bipolar impedance vectors and a left ventricular lead. FIGS. 9 and 10 illustrate that position 2 has a larger time difference between start of contraction in the right ventricle and the timing of the local contraction at position 2 as compared to position 1 both for intrinsic and paced cardiac cycles. FIG. 11 illustrates the mean maximum dP/dt determined when pacing at position 1 and 2 of the left ventricle. Maximum dP/dt is an index that is used clinically to characterize contractility ability of the heart. Generally, subjects having disorders of the left ventricular myocardium have lower maximum dP/dt as compared to healthy subjects. As is clearly seen from the figure, position 2 having larger time difference than position 1 results in better cardiac function as assessed by the median maximum dP/dt. FIG. 12 graphically illustrates the median time difference determined for position 1 and position 2 for intrinsic cardiac cycles. It is clear from this figure that local myocardial contraction occurs later at position 2 than in position 1 when compared to the same reference start time coinciding with right ventricular contraction.

Figures 6, 7, 8:
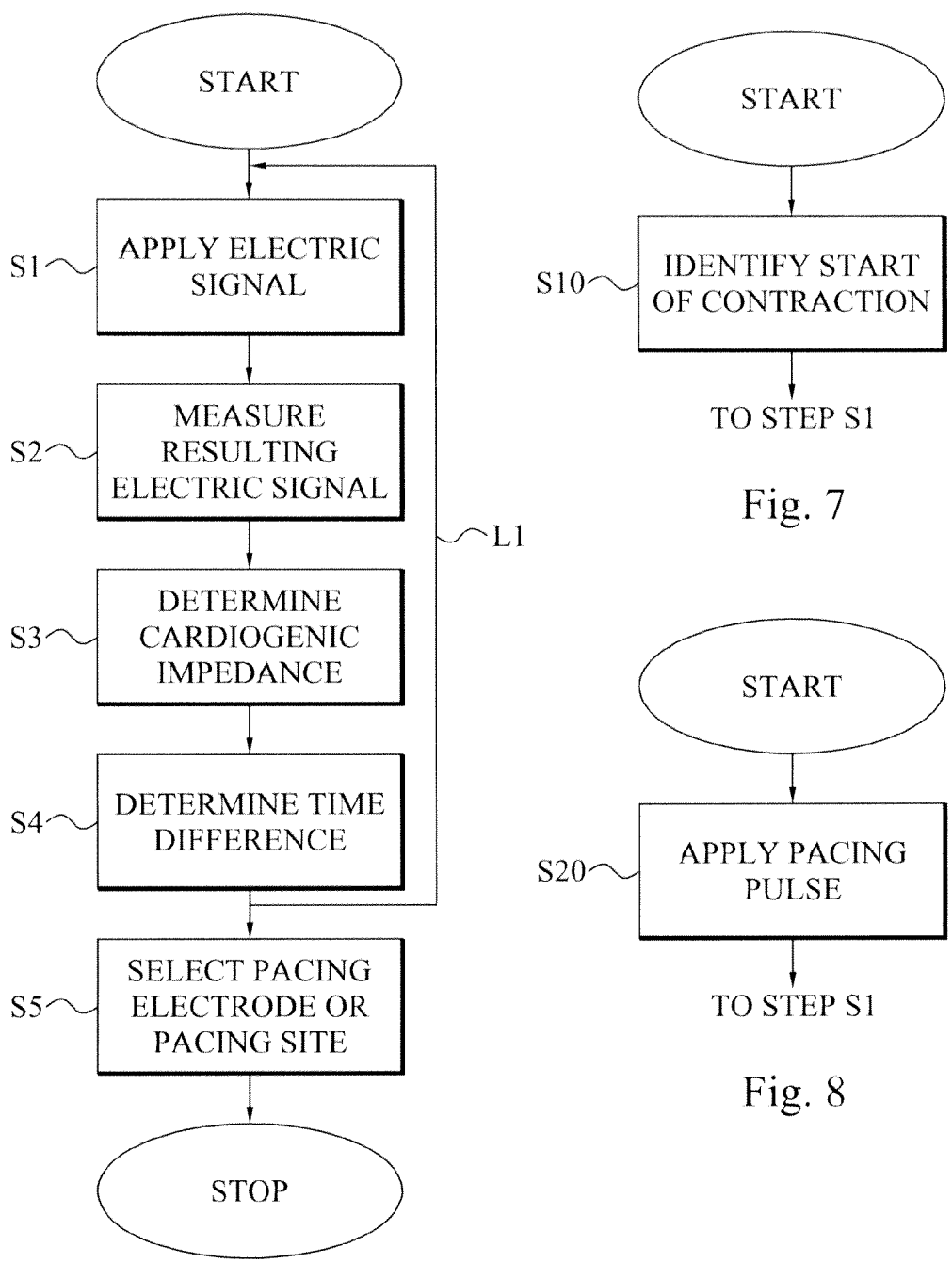
FIG. 6 is a flow diagram illustrating an embodiment of a method of identifying pacing site for a ventricle.
FIG. 7 is a flow diagram illustrating an additional step of the method in FIG. 6 according to an embodiment.
FIG. 8 is a flow diagram illustrating an additional step of the method in FIG. 6 according to another embodiment.

FIG. 6 is a flow diagram illustrating a method of identifying pacing site for a first ventricle of a heart in a subject. The method starts in step S1 where an electric signal is applied over two neighboring electrodes of a first ventricular lead positioned in or in connection with the first ventricle or over an electrode of the first ventricular lead and a case electrode of an IMD to which the first ventricular lead is connected. A resulting electric signal is sensed and measured over a candidate pair of neighboring electrodes of the first ventricular lead or over a candidate electrode of the first ventricular lead and the case electrode in step S2. A next step S3 determines an impedance signal, preferably cardiogenic impedance signal, representative of and capturing local myocardial contraction at a ventricular site associated with and present in vicinity of the candidate pair or candidate electrode. A time difference between start of contraction within a second ventricle of the heart and the timing of local myocardial contraction at the ventricular site of the candidate pair or candidate electrode as identified from the impedance signal from step S3 is determined in step S4.

Steps S1-S4 are repeated for each candidate pair or candidate electrode or for each site of the candidate pair or candidate electrode, which is schematically illustrated by the line L1. The loop S1-S4 can be repeated for each candidate pair or electrode. Alternatively, all candidate pairs or electrodes or at least a portion thereof are assessed simultaneously using different frequencies as previously described.

The method as illustrated in FIG. 6 can be conducted in connection with implantation of the first ventricular lead or after implantation. In the former case, the first ventricular lead can be positioned at a first site in or in connection with the first ventricle. The procedure of steps S1-S4 is then conducted for at least one candidate pair or candidate electrode at this site of the lead. Next the physician moves the ventricular lead to another site in or in connection with the first ventricle and the procedure of steps S1-S4 is repeated for this new site.

Steps S1 to S4 can also be conducted for each of the multiple candidate pairs or candidate electrodes without moving the first ventricular lead or after the lead has been moved to optimal site. The procedure can therefore be conducted both in connection with implantation but also any time after implantation.

Finally, step S5 selects the pacing site for the first ventricle to correspond to the site associated with the candidate pair having largest time difference, the site of the candidate electrode having largest time difference of corresponding to the site of multiple different lead sites resulted in largest time difference.

For instance and in connection with implantation, a fixed candidate pair or fixed candidate electrode can be used in steps S1-S4 but different lead sites are tested to select the optimal lead site for this fixed candidate pair or candidate electrode. This means that the same candidate pair or candidate electrode of the first ventricular lead is initially used for each loop of steps S1-S4 and the only difference is the position of the first ventricular lead in or in connection with the first ventricle. Once optimal lead site has been found, steps S1-S4 can be performed for all available candidate pairs and candidate electrodes of the first ventricular lead. In such case, both optimal lead site and optimal pacing electrode can be found.

FIG. 7 is a flow diagram illustrating an additional step of the method in FIG. 6. The method starts with step S10 where start of contraction within the second ventricle of the heart is identified based on a signal sensed by a second ventricular lead positioned in or in connection with the second ventricle. The sensed signal can for instance be representative of electrical activity of the second ventricle or a resulting electric signal to be used for deriving an impedance signal reflecting and capturing contraction of the second ventricle. This start of contraction as determined from the sensed signal is then used in step S4 when determining the time difference. The method then continues to step S1 of FIG. 6. In an embodiment, the signal sensing conducted in step S10 to identify start of contraction is preferably performed at least partly in parallel with step S2 of FIG. 6.

FIG. 8 is a flow diagram illustrating an additional step of the method in FIG. 6. The method starts in step S20 where a pacing pulse is applied to the second ventricle using at least one electrode of the second ventricular lead to thereby trigger contraction within the second ventricle. The time difference determined in step S4 between the start of contraction within the second ventricle and the timing of local myocardial contraction at the site in the left ventricle can then be defined from the timing of generating/applying the pacing pulse to the second ventricle to the timing of local myocardial contraction in the first ventricle. The method then continues to step S1 of FIG. 6.

Although modifications and changes may be suggested by those skilled in the art, it is the intention of the inventors to embody within the patent warranted hereon all changes and modifications as reasonably and properly come within the scope of their contribution to the art.

We claim as our invention:

1. An implantable medical device comprising:
   a first ventricular lead having multiple electrodes;
   a second ventricular lead having at least one electrode, said first ventricular lead is constructed to be implantable in or in connection with a first ventricle of a heart and said second ventricular lead is constructed to be implantable in or in connection with a second ventricle of said heart;
   a signal generator coupled to said first and second ventricular leads and configured to generate an electric signal applicable over two neighboring electrodes of said first ventricular lead or over an electrode of said first ventricular lead and a case electrode of said implantable medical device;
   a signal sensing unit configured to sense, for each candidate pair of neighboring electrodes of said first ventricular lead or for each candidate electrode of said first ventricular lead, a resulting electric signal over said candidate pair of neighboring electrodes or over said candidate electrode and said case electrode;
   an impedance processor configured to determine, for each candidate pair or for each candidate electrode, an impedance signal representative of local myocardial contraction at a site of said first ventricle associated with said candidate pair or said candidate electrode based on said electric signal and said resulting electric signal sensed by said signal sensing unit for said candidate pair or said candidate electrode;
   a time processor configured to determine, for each candidate pair or each candidate electrode, a time difference between start of contraction within said second ventricle and a timing of said local myocardial contraction at said site associated with said candidate pair or said candidate electrode based on said impedance signal; and
   an electrode selector configured to select a pacing electrode for said first ventricle corresponding to one of the electrodes of the candidate pair having largest time difference or corresponding to the candidate electrode having largest time difference.

2. The implantable medical device according to claim 1, further comprising a signal processing unit configured to identify start of contraction within said second ventricle based on a signal sensed by said second ventricular lead.

3. The implantable medical device according to claim 2, wherein said signal processing unit is configured to identify said start of contraction based on a signal representative of cardiac activity of said heart sensed by said second ventricular lead.

4. The implantable medical device according to claim 2, further comprising a pulse generator configured to generate pacing pulses to be applied by said second ventricular lead to said second ventricle, wherein
   said signal sensing unit is configured to i) sense, for each candidate pair or for each candidate electrode and for at least one paced cardiac cycle for which said pulse generator generates pacing pulses, a first resulting electric signal over said candidate pair of neighboring electrodes or over said candidate electrode and said case electrode and ii) sense, for each candidate pair or for each candidate electrode and for at least one intrinsic cardiac cycle for which said pulse generator does not generate any pacing pulses, a second resulting electric signal over said candidate pair of neighboring electrodes or over said candidate electrode and said case electrode;
   said impedance processor is configured to determine, for each candidate pair or each candidate electrode, i) a first impedance signal representative of local myocardial contraction at said site of said first ventricle associated with said candidate pair or said candidate electrode for a paced cardiac cycle based on said electric signal and said first resulting electric signal sensed by said signal sensing unit for said candidate pair or said candidate electrode and ii) a second impedance signal representative of local myocardial contraction at said site of said first ventricle associated with said candidate pair or said candidate electrode for an intrinsic cardiac cycle based on said electric signal and said second resulting electric signal sensed by said signal sensing unit for said candidate pair or said candidate electrode;
   said time processor is configured to determine, for each candidate pair or each candidate electrode, i) a paced time difference between start of contraction within said second ventricle and a timing of said local myocardial contraction at said site associated with said candidate pair or said candidate electrode for said paced cardiac cycle and ii) a spontaneous time difference between start of contraction within said second ventricle and a timing of said local myocardial contraction at said site associated with said candidate pair or said candidate electrode for said intrinsic cardiac cycle; and
   said electrode selector is configured to select i) a pacing electrode for said first ventricle to use for paced cardiac cycles corresponding to one of the electrodes of the candidate pair having largest paced time difference or corresponding to the candidate electrode having largest paced time difference and ii) select a pacing electrode for said first ventricle to use for intrinsic cardiac cycles corresponding to one of the electrodes of the candidate pair having largest spontaneous time difference or corresponding to the candidate electrode having largest spontaneous time difference.

5. The implantable medical device according to claim 1, further comprising a pulse generator configured to generate a pacing pulse applicable to an electrode of said second ventricular lead to trigger contraction within said second ventricle.

6. The implantable medical device according to claim 1, wherein said signal sensing unit is configured to sense, for each cardiac cycle of multiple cardiac cycles, a resulting electric signal over a candidate pair of neighboring electrodes of said first ventricular lead or over a candidate electrode of said first ventricular lead and said case electrode, wherein said candidate pair or said candidate electrode employed in a first cardiac cycle of said multiple cardiac cycles is different from said candidate pair or said candidate electrode employed in a second cardiac cycle of said multiple cardiac cycles.

7. The implantable medical device according to claim 1, wherein
   said first ventricular lead is a quadropolar ventricular lead comprising four electrodes;
   said signal generator is configured to generate, for each candidate pair of neighboring electrodes of said quadropolar ventricular lead, an electric signal applicable over said candidate pair of neighboring electrode;
   said signal sensing unit is configured to sense, for each candidate pair, a resulting electric signal over said candidate pair of neighboring electrodes;
   said impedance processor is configured to determine, for each candidate pair, an impedance signal representative of local myocardial contraction at a site of said first ventricle associated with said candidate pair based on said electric signal and said resulting electric signal sensed by said signal sensing unit for said candidate pair;

said time processor is configured to determine, for each candidate pair, a time difference between start of contraction within said second ventricle and a timing of said local myocardial contraction at said site associated with said candidate pair; and said electrode selector is configured to select a pacing electrode for said first ventricle corresponding to one of the electrodes of the candidate pair having largest time difference.

8. The implantable medical device according to claim 1, wherein said signal generator is configured to generate, for each candidate electrode of said first ventricular lead, an electric signal applicable over said candidate electrode and said case electrode;

said signal sensing unit is configured to sense, for each candidate electrode, a resulting electric signal over said candidate electrode and said case electrode;

said impedance processor is configured to determine, for each candidate electrode, an impedance signal representative of local myocardial contraction at a site of said first ventricle associated with said candidate electrode based on said electric signal and said resulting electric signal sensed by said signal sensing unit for said candidate electrode;

said time processor is configured to determine, for each candidate electrode, a time difference between start of contraction within said second ventricle and a timing of said local myocardial contraction at said site associated with said candidate electrode; and said electrode selector is configured to select the candidate electrode having largest time difference as pacing electrode for said first ventricle.

9. The implantable medical device according to claim 1, wherein said first ventricular lead is a quadropolar ventricular lead comprising four electrodes;

said signal generator is configured to generate, for each candidate pair of neighboring electrodes of said quadropolar ventricular lead, an electric signal applicable over an electrode of said quadropolar ventricular lead and said case electrode, wherein said electrode of said quadropolar ventricular lead does not form part of said candidate pair;

said signal sensing unit is configured to sense, for each candidate pair, a resulting electric signal over said candidate pair of neighboring electrodes;

said impedance processor is configured to determine, for each candidate pair, an impedance signal representative of local myocardial contraction at a site of said first ventricle associated with said candidate pair based on said electric signal and said resulting electric signal sensed by said signal sensing unit for said candidate pair;

said time processor is configured to determine, for each candidate pair, a time difference between start of contraction within said second ventricle and a timing of said local myocardial contraction at said site associated with said candidate pair; and said electrode selector is configured to select a pacing electrode for said first ventricle corresponding to one of the electrodes of the candidate pair having largest time difference.

10. The implantable medical device according to claim 1, further comprising a threshold measuring unit configured to measure a respective pacing threshold for each electrode of said candidate pair having largest time difference, wherein said electrode selector is configured to select said pacing electrode for said first ventricle corresponding to the electrode that has the lowest pacing threshold of said candidate pair having largest time difference.

11. A method of identifying a pacing site for a first ventricle of a heart comprising the steps:

i) applying an electric signal over two neighboring electrodes of a first ventricular lead having multiple electrodes and being positioned in or in connection with said first ventricle or over an electrode of said first ventricular lead and a case electrode of an implantable medical device to which said first ventricular lead is connected;

ii) sensing a resulting electric signal over a candidate pair of neighboring electrodes of said first ventricular lead or over a candidate electrode of said first ventricular lead and said case electrode;

ii) determining an impedance signal representative of local myocardial contraction at a site of said first ventricle associated with said candidate pair or said candidate electrode based on said electric signal and said resulting electric signal;

iv) determining a time difference between start of contraction within a second ventricle of said heart and a timing of said local myocardial contraction at said site associated with said candidate pair or said candidate electrode based on said impedance signal;

v) repeating the steps i) to iv) for a different candidate pair of neighboring electrodes, a different candidate electrode or for a different site of said candidate pair or said candidate electrode in or in connection with said first ventricle;

vi) selecting a pacing site for said first ventricle corresponding to the site associated with the candidate pair having largest time difference, corresponding to the site associated with the candidate electrode having largest time difference or corresponding to the site of the different sites resulted in largest time difference.

12. The method according to claim 11, further comprising identifying start of contraction within said second ventricle based on a signal sensed by a second ventricular lead positioned in or in connection with said second ventricle and connected to said implantable medical device.

13. The method according to claim 11, further comprising applying a pacing pulse to an electrode of a second ventricular lead position in or in connection with said second ventricle and connected to said implantable medical device to trigger contraction within said second ventricle.

14. The method according to claim 11, wherein step iv) comprises determining said time difference between start of contraction for a cardiac cycle within said second ventricle and a timing of said local myocardial contraction for said cardiac cycle at said site associated with said candidate pair or said candidate electrode.

* * * * *